（12）United States Patent
Shiuey (10) Patent No.: US 8,029,515 B2
(45) Date of Patent: Oct. 4, 2011

(54) CORNEAL IMPLANTS AND METHODS AND SYSTEMS FOR PLACEMENT

(75) Inventor: Yichieh Shiuey, Cupertino, CA (US)

(73) Assignee: Yichieh Shiuey, San Jose, CA (US)

( * ) Notice: Subject to any disclaimer, the term of this patent is extended or adjusted under 35 U.S.C. 154(b) by 319 days.

(21) Appl. No.: 11/741,496

(22) Filed: Apr. 27, 2007

(65) Prior Publication Data

US 2007/0244559 A1    Oct. 18, 2007

Related U.S. Application Data

(63) Continuation-in-part of application No. 11/341,320, filed on Jan. 26, 2006, now abandoned.

(60) Provisional application No. 60/648,949, filed on Jan. 31, 2005.

(51) Int. Cl.
*A61F 9/00* (2006.01)
(52) U.S. Cl. ............................. 606/107; 623/5.11
(58) Field of Classification Search .................. 606/107; 623/5.11, 6.12
See application file for complete search history.

(56) References Cited

U.S. PATENT DOCUMENTS

| | | | |
|---|---|---|---|
| 4,706,666 A | 11/1987 | Sheets | |
| 4,919,130 A | 4/1990 | Stoy et al. | |
| 5,211,660 A | 5/1993 | Grasso | |
| 5,269,812 A * | 12/1993 | White | 128/898 |
| 5,300,116 A | 4/1994 | Chirila et al. | |
| 5,344,449 A | 9/1994 | Christ et al. | |
| 5,474,562 A * | 12/1995 | Orchowski et al. | 606/107 |
| 5,702,441 A | 12/1997 | Zhou | |
| 5,868,752 A | 2/1999 | Makker et al. | |
| 5,919,197 A | 7/1999 | McDonald | |
| 6,050,999 A | 4/2000 | Paraschac et al. | |
| 6,162,229 A | 12/2000 | Feingold et al. | |
| 6,454,800 B2 | 9/2002 | Dalton et al. | |
| 6,579,918 B1 | 6/2003 | Auten et al. | |
| 6,626,941 B2 | 9/2003 | Nigam | |
| 6,689,165 B2 | 2/2004 | Jacob et al. | |
| 6,712,848 B1 | 3/2004 | Wolf et al. | |
| 6,786,926 B2 | 9/2004 | Peyman | |
| 6,855,163 B2 | 2/2005 | Peyman | |
| 6,858,033 B2 | 2/2005 | Kobayashi | |
| 6,976,997 B2 | 12/2005 | Noolandi et al. | |
| 7,276,071 B2 * | 10/2007 | Lin et al. | 606/107 |
| 2002/0022881 A1 | 2/2002 | Figueroa et al. | |
| 2002/0055753 A1 | 5/2002 | Silvestrini | |
| 2003/0025873 A1 | 2/2003 | Ocampo | |
| 2003/0050646 A1 * | 3/2003 | Kikuchi et al. | 606/107 |
| 2003/0054109 A1 | 3/2003 | Quinn et al. | |

(Continued)

OTHER PUBLICATIONS

International Search Report and Written Opinion of PCT Application No. PCT/US06/02918, dated May 1, 2008, 11 pages total.

(Continued)

*Primary Examiner* — S. Thomas Hughes
*Assistant Examiner* — Sarah A Simpson
(74) *Attorney, Agent, or Firm* — Wilson Sonsini Goodrich & Rosati (57) ABSTRACT

A system comprising a hollow member is used to deliver a constrained corneal implant into a corneal pocket. The hollow member may be tapered and the system may further include an implant deformation chamber and an axial pusher to advance the implant through the hollow member.

12 Claims, 12 Drawing Sheets

U.S. PATENT DOCUMENTS

| | | |
|---|---|---|
| 2003/0093083 A1 | 5/2003 | Peyman |
| 2003/0173691 A1 | 9/2003 | Jethmalani et al. |
| 2004/0199174 A1* | 10/2004 | Herberger et al. ............ 606/107 |
| 2004/0243159 A1 | 12/2004 | Shiuey |
| 2004/0243160 A1 | 12/2004 | Shiuey et al. |
| 2006/0235430 A1 | 10/2006 | Le et al. |
| 2006/0252981 A1 | 11/2006 | Matsuda et al. |

OTHER PUBLICATIONS

International Search Report and Written Opinion of PCT Application No. PCT/US08/61656, dated Sep. 16, 2008, 9 pages total.

Final Rejection of U.S. Appl. No. 11/341,320, mailed Nov. 19, 2009, 12 page total.

* cited by examiner

CORNEAL IMPLANTS AND METHODS AND SYSTEMS FOR PLACEMENT

CROSS-REFERENCES TO RELATED APPLICATIONS

The present application is a continuation-in-part of U.S. application Ser. No. 11/341,320, filed on Jan. 26, 2006, which claims the benefit of Provisional Application No. 60/648,949, filed Jan. 31, 2005, the full disclosures of which are incorporated herein by reference.

BACKGROUND OF THE INVENTION

Field of the Invention

There are many different types of corneal implants that have been developed for the treatment of refractive error and disease. Because of limitations in the methods of creating corneal pockets, these implants have all been designed for placement in the cornea by creation of a corneal incision which is either similar in size to the smallest dimension of the implant or larger. Recently, two methods of corneal pocket creation have been devised which can create a pocket with an external opening width that is less than the maximum internal width of the pocket. These two methods are pocket creation by the femtosecond laser and, of particular interest, cornea cutting, as described in US 2004/0243159 and 0243160, invented by the inventor herein, the full disclosure of which is incorporated herein by reference.

It is advantageous to have a biocompatible corneal implant that can be placed through an external incision that is less than the width of the implant, especially an external incision that is less than half of the width of the implant. A small external incision decreases induced surgical astigmatism and speeds up the recovery time for the patient. Moreover, it is useful to have a relatively large implant that can be placed through a relatively small incision. For example a lens implant that is larger is more likely to give good quality vision especially in a patient with large pupils. It is also advantageous to have a simple and reliable delivery system for the corneal implant.

Intraocular lenses for cataract surgery have been designed to be placed through a small incision. These small incision cataract surgery lenses cannot practically be used within a corneal pocket. Most small incision cataract surgery lens implants are usually too thick to be placed within a corneal pocket. For example the typical thickness of a cataract surgery lens implant is 1 mm or more which is substantially thicker than the human cornea, which is usually between 0.5 to 0.6 mm. Some corneal implants that have been designed only have a thickness of about 0.05 mm. Moreover, the cataract surgery lens implants have haptics, which are extensions from the lens implant designed to keep the lens implant fixated within the capsular bag. Haptics are not present and not necessary for corneal implants. Finally, the cataract surgery lens implants are not designed to be biocompatible with the cornea and would not be tolerated as corneal implants.

The delivery systems designed for small incision cataract surgery lens implants are not well adapted for use as a delivery system for small incision corneal implants. These delivery systems have been designed for cataract surgery lens implants that are much thicker than the usual corneal implant. The delivery systems for small incision cataract surgery lens implants are designed to accommodate haptics, which would not be present on a corneal lens implant.

Corneal implants can be made of either synthetic materials (e.g. prostheses) or can be biological in origin (e.g. transplant grafts). Recently two new surgical techniques for placement of a lamellar corneal stromal endothelial transplant grafts have been devised. These surgical techniques are useful in the treatment of endothelial diseases of the cornea such as Fuchs' endothelial dystrophy and pseudophakic bullous keratopathy. One of these techniques is referred to as deep lamellar endothelial keratoplasty (DLEK). In this technique a pocket is made within the cornea and diseased corneal endothelium is excised along with a layer of corneal stroma. Healthy lamellar corneal stromal endothelial tissue is then transplanted into the space left by the excised diseased tissue. Another technique is called Descemet's stripping automated endothelial keratoplasty (DSAEK). In this technique, a lamellar corneal stromal endothelial transplant graft is automatically created using either a microkeratome or a laser. The diseased corneal endothelium is stripped away with surgical instruments and then the lamellar corneal stromal endothelial transplant graft is inserted into the anterior chamber through a full thickness corneal incision. The graft is then held in place against the stripped posterior corneal stromal surface by an air bubble until the graft is able to heal in position.

In both DLEK and DSAEK it is advantageous to be able to insert a relatively large transplant atraumatically through a small corneal or scleral incision. A larger transplant has more corneal endothelial cells and should produce better results in the treatment of corneal endothelial diseases. However, a significant problem with prior art methods of inserting corneal transplants into the anterior chamber through a small incision is that they all involve folding of the transplant and grasping of the transplant with forceps. Moreover, the transplant is typically severely compressed as it passes through the corneal incision. It has been demonstrated through the use of vital staining techniques that many of the delicate corneal endothelial cells of a transplant are killed during the prior art insertion process. Like corneal transplant grafts for DSAEK or DLEK, synthetic corneal implants e.g. corneal inlay prostheses are also very delicate. In many cases, these corneal inlays may be as thin as 30 to 40 microns, which make them very easily torn by forceps. Therefore, there is also a need for an improved method to place these corneal inlays atraumatically through a small incision.

Delivery systems for placement of intraocular lenses (IOLs) into the posterior chamber through a small incision have been described. However, these delivery systems designed for small incision cataract surgery IOLs are not well adapted for use as a delivery system for corneal implants through a small incision. For example, a typical intraocular lens implant may be 1 mm or more in thickness, whereas the typical corneal transplant for DLEK or DSAEK is between 0.1 to 0.15 mm in thickness. Moreover, as has been noted before, the thickness of a corneal inlay prosthesis may be as little as 30 to 40 microns. In addition, the size and shape of an IOL is different from that of a corneal transplant. An IOL is typically 12 to 13 mm in length and 5 to 6 mm wide, whereas a corneal transplant would typically be circular in shape and would have a diameter of 8 to 9 mm. In the case of a corneal prosthesis inlay, the diameter may range from 1 mm to 10 mm. Finally, IOL delivery systems are designed to greatly compress the IOL during the insertion process, whereas this type of compression would be likely to either damage or destroy a living corneal transplant. The amount of compression used for IOL delivery systems could also damage the much thinner corneal implants.

BRIEF SUMMARY OF THE INVENTION

Improved systems and methods for implanting corneal implants are provided by the present invention. The phase "corneal implant" refers to any natural (biological) or synthetic implant or graft that may be implanted into a human cornea. These systems and methods can place a corneal implant through a corneal incision that is substantially less than the width of the implant. The placement of the implant may be within or between any of the layers of the cornea including epithelium, Bowman's membrane, stroma, Descemet's membrane, and endothelium. In preferred aspects, the corneal incision is equal or less than half of the width of the implant. In additional preferred aspects, the system allows the placement of a corneal implant through an incision that is less than or equal to 3 mm, which advantageously avoids the need for suturing of the incision in most cases and also greatly decreases the chance of unwanted induced astigmatism.

In accordance with a first aspect of the present invention, the corneal implant is reversibly deformable in shape to allow its passage through a corneal incision that is equal or less than half of the width of the implant. The corneal implant is biocompatible with the cornea, the eye, and the body. In certain embodiments, synthetic material which can meet these criteria may potentially be used for the implant. Suitable synthetic materials include one or more compounds selected from the group consisting of collagen, polyurethanes, poly(2-hydroxyethylmethacrylate), polyvinylpyrolidone, polyglycerolmethacrylate, polyvinyl alcohol, polyethylene glycol, polymethacrylic acid, silicones, acrylics, polyfluorocarbons, and polymers with phosphocholine. In other embodiments, the grafts may comprise human corneas harvested for use in transplants. In the future, biological cornea implants may be obtained from other sources such as animals, genetically modified animals, in vitro cell culture, or the like.

In a preferred embodiment, the material comprises a hydrogel. In additional preferred embodiments, the material comprises polymethacrylic acid-co hydroxyethyl methacrylate (PHEMA/MAA). In other preferred embodiments, holes or pores may be provided in the implant to increase biocompatibility of the implant by allowing nutritive substances and gasses (e.g., water, glucose, and oxygen) to pass easily through the implant in order to maintain healthy metabolism in the cornea. In still other preferred embodiments, the polymer material may have thermoplastic properties such that the implant will have one desired shape at one temperature and then deform into another desired shape at a second temperature. In yet other preferred aspects, the corneal implant may comprise one or more separate, smaller components that can be assembled in situ placed inside the corneal pocket. Such in situ assembly advantageously minimizes the incision size needed to insert a corneal implant.

The corneal implant may be of any shape that allows it to be placed within a corneal pocket. In preferred embodiments, the corneal implant is substantially round. In alternate preferred embodiments, the corneal implant is not round. A corneal implant which is not round has the advantage that it is less likely to rotate within a corneal pocket. This property is useful in the implants which correct for astigmatism.

In preferred other embodiments, the corneal implant is a lens. The lens can be a monofocal, multifocal, Fresnel, diffractive, prismatic, or other type of lens that can be used to treat refractive error (such as myopia, hyperopia, or astigmatism) presbyopia, or ocular disease e.g. macular degeneration. The lens may also be made of a polymer that can have its refractive properties adjusted permanently or reversibly by electromagnetic energy as described in U.S. Patent Application 2003/0173691 to Jethmalani.

The corneal implant usually comprises a prosthesis that is used to replace or augment a portion of the cornea. Such implants are useful in restoring optical clarity or structural integrity to the cornea in lieu of corneal transplantation. The corneal prosthesis may be used to replace only a partial thickness portion of the cornea or a full thickness portion of the cornea. In preferred aspects, the corneal implant may be coated with extracellular matrix proteins such as collagen, fibronectin, laminin, substance P, insulin-like growth factor-1, or peptide sequences such as fibronectin adhesion-promoting peptide (FAP). In additional preferred aspects, these extracellular matrix proteins and peptides are tethered or otherwise bound to the epithelial side of the corneal implant by the methods described in U.S. Pat. No. 6,689,165, to Jacob et al. Such surface treatments are intended to promote epithelialization on the surface of a corneal implant.

In alternate preferred embodiments, the surface of the corneal implant may have a texture that promotes epithelialization on the surface of the corneal implant. Textures, such as surface indentations, may be applied to the surface of the corneal implant to promote epithelialization, as described in U.S. Pat. No. 6,454,800 to Dalton et al.

In yet other alternate preferred embodiments, the corneal implant may be manufactured from a material that promotes epithelialization on the surface of the corneal implant. Examples of such materials include polymers selected from the group consisting of collagen and N-isopropylacrylamide, collagen and 1-ethyl-3,3'(dimethyl-aminopropyl)-carbodiimide as well as collagen and N-hydroxysuccinimide (EDC/NHS). In further preferred aspects, the polymer may additionally contain extracellular matrix proteins such as fibronectin, laminin, substance P, insulin-like growth factor-1, or peptide sequences such as fibronectin adhesion-promoting or peptide (FAP).

Optionally, at least a portion of the device may contain holes or be porous in nature so as to promote growth of corneal tissue into and through the implant in order to promote retention and biocompatibility. Such porous implants may be fabricated as described in U.S. Pat. No. 6,976,997 to Noolandi et al. and U.S. Pat. No. 5,300,116 to Chirila et al.

Optionally, at least a portion of the lens or other corneal implant may be colored. Coloration can be useful for cosmetic purposes or for therapeutic purposes e.g. treatment of aniridia. For example, methods of applying biocompatible inks, which are well known in colored contact lens manufacturing, may be used to color the corneal implant. Particular coloring methods are described in U.S. Patent Applications 2003/0054109 and 2003/0025873, the disclosures of which are incorporated herein by reference. In alternate preferred aspects, the corneal implant may be colored with photosensitive inks that change color with exposure to electromagnetic waves. This allows the color of the corneal implant to be adjusted permanently or reversibly by exposure to electromagnetic waves in vivo.

Optionally, the corneal implant may also contain an ultraviolet filter compound of the benzophenone type such as 3-(2 Benzyotriazolyl)-2-Hydroxy-5-Tert-Octyl-Benzyl Methacryl Amide.

In yet other alternate preferred embodiments, the corneal implant may be a device. Examples of potential implant devices include miniature cameras and aqueous glucose monitors.

The improved corneal implants of the present invention are deformable into a reduced width shape that allows passage through a corneal incision that is substantially less than the width of the implant when undeformed or unconstrained. In preferred aspects, the incision will be less than or equal to one-half of the width of the implant.

A system according to the present invention comprises a hollow member and implant mover or other axial pusher used to deliver a corneal implant that has been constrained to fit inside an axial hollow passage of the hollow member. The implant may be deformed or constrained in any shape or configuration having a "reduced width" that allows it to be fit inside of the hollow member e.g., rolled or folded. By "reduced width" it is meant that a maximum width of the implant, such as a diameter of a circular lens, is reduced by some threshold amount, typically by at least one-half (50%), often by at least 60%, and sometimes by 65% or more.

A system according to the present invention comprises a hollow member and implant mover used to deliver a corneal implant that has been restrained to fit inside of the hollow member. Once the corneal implant is inside the hollow member, the implant mover is used to move the implant into a corneal pocket or the anterior chamber.

Optionally, the system may further comprise a deformation chamber where the implant is deformed into a shape and size that will fit inside the hollow member. In preferred aspects, the deformation chamber may contain ridges, protrusions, indentations, or recesses which help to maintain and guide the orientation of the corneal implant within the deformation chamber during the deformation process. In further preferred aspects the deformation chamber will be a size that is appropriate for the type of corneal implant which is being used. For example in the case of a corneal transplant, the minimum internal dimensions of an open deformation chamber should be between 6 and 10 mm, more preferably between 8 and 9 mm. In the case of a corneal implant prosthesis, the minimum internal dimensions of an open deformation chamber dimensions should be between 1 mm and 10 mm, more preferably between 2.0 mm and 7 mm. In additional preferred aspects the deformation area may be tapered or funnel shaped, i.e. narrower one end than on the other end. The tapered or funnel shape advantageously facilitates the corneal implant to be restrained to a smaller diameter configuration.

In other preferred aspects, the interior of the hollow member may contain ridges, protrusions, indentations, or recesses which help to maintain and guide the orientation of the corneal implant as it travels inside of the hollow member. In additional preferred aspects, the interior of the hollow member may contain ridges, protrusions, indentations, or recesses which guides a lamellar corneal stromal endothelial transplant to deform in a way which allows it to travel through a small incision without the need for folding or being grasped by forceps. The system is designed to allow a corneal transplant to be placed through an incision equal or less than 3 mm. However, the system can also be used to place an implant through an incision that is greater than 3 mm.

Optionally, the system may be designed to be sterile and disposable for single use. This advantageously decreases the chance for contamination and infection. It also obviates the need for the surgeon to autoclave or to provide other methods of sterilization such as ethylene oxide. To insure that the system will be both sterile and single use only we can add one or more of the following features. In preferred aspects one or more components of the system may be made of a polymer which will melt or deform into an unusable shape upon autoclaving. In additional preferred aspects, the system may have a one way locking mechanism, such that once the tip of the implant mover travels to a certain distance, the implant mover is locked in position inside of the hollow member, thus preventing reloading of another corneal implant. In alternative preferred aspects, the system may be assembled through the use of breakable tabs or snaps, which allows the secure assembly of the disposable component, but which are easily destroyed if there is an attempt to disassemble the system for reuse.

Optionally, the system may be designed so that the corneal implant is pre-loaded inside of the hollow member prior to use by the surgeon. This advantageously minimizes the need for manipulation of the delicate corneal implant by the surgeon, which could result in damage to the corneal implant.

Once the corneal implant is inside the hollow member, the implant mover or other axial pusher is used to engage and push the implant into the corneal pocket. Optionally, the system may further comprise a deformation chamber where the implant is deformed into a shape and size that will fit inside the hollow member. In other preferred aspects, the deformation chamber may contain ridges, protrusions, indentations, or recesses which help to maintain orientation of the corneal implant within the deformation chamber during the deformation process. Optionally, the hollow member is tapered, i.e., narrower at a distal end than at a proximal end. Such tapering allows additional deformation (size or width reduction) of the implant as it is advanced through the hollow member and passes out through a smaller distal opening. The interior of the hollow member may contain ridges, protrusions, indentations, or recesses which help to maintain orientation of the corneal implant as it travels inside of the hollow member. The system for implant placement is designed to allow an implant to be placed into a corneal pocket with an entry incision that is equal or less than one-half of the width of the implant, however, the system can also be used to place an implant through a corneal incision that is greater than one-half of the width of the implant.

DETAILED DESCRIPTION

Figure 1A:
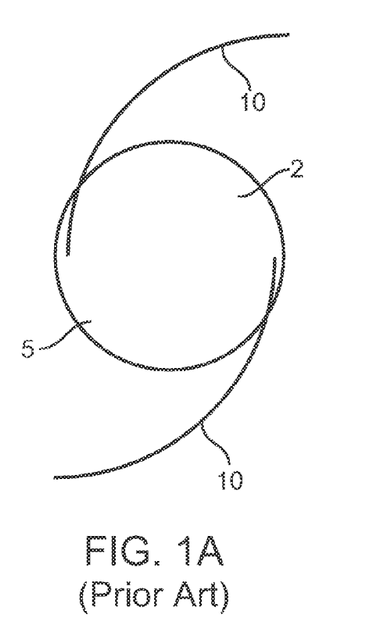
FIGS. 1A, 1B, 1C, and 1D illustrate prior art corneal implants.
Figure 1B:
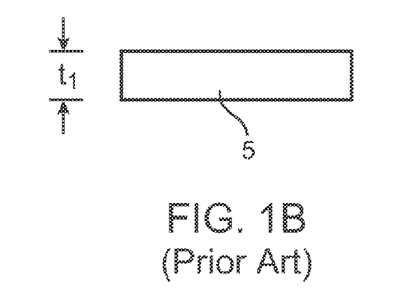
Figure 1C:
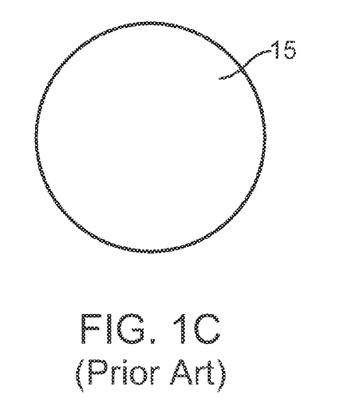
Figure 1D:
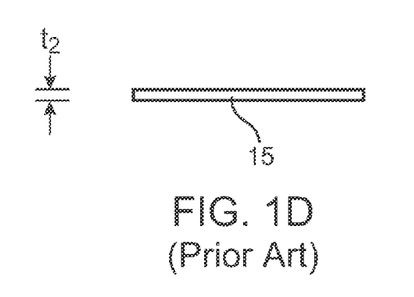

FIG. 1A shows a top view of a cataract surgery lens implant 2. A round optic 5 of the implant 2 has haptics 10 which extend from the periphery of the optic. The haptics 10 are used to help the optic center and fixate within the capsular bag. FIG. 1B shows a side view of a cataract surgery lens implant optic 5. Note that the thickness $t_1$ of the optic 5 is typically 1 mm or more and is substantially greater than the 0.5 to 0.6 mm thickness of the human cornea. The thickness of the optic 5 makes it inappropriate for use as a corneal lens implant. FIG. 1C shows a top view of a corneal implant 15. Note there are no haptics on the corneal implant. FIG. 1D shows a side view of corneal implant 15. Note that the thickness $t_2$ is substantially less than cataract surgery lens implant 5. The thickness $t_2$ of corneal implant 15 would in general be less than the thickness of the human cornea.

Figure 2A:
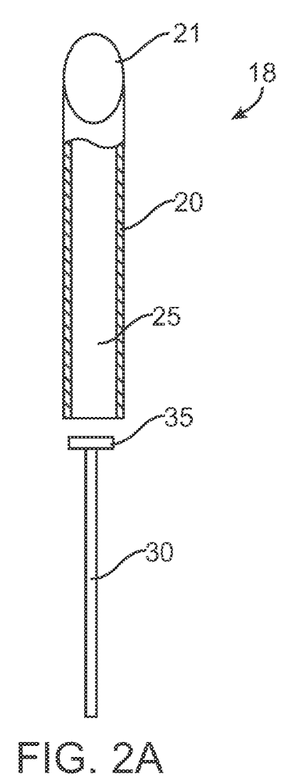
FIGS. 2A through 2C illustrates a first embodiment of apparatus of the present invention.
Figure 2B:
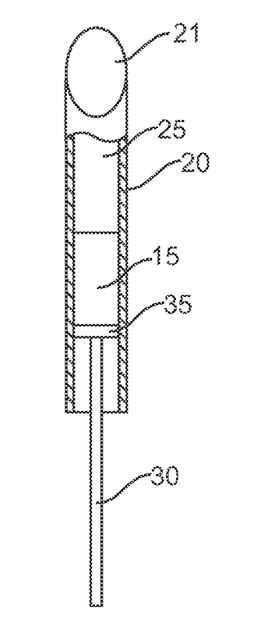
Figure 2C:
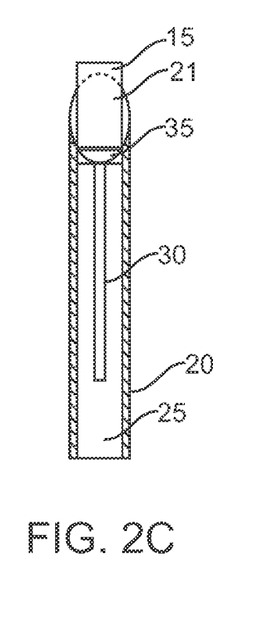

FIG. 2A shows a corneal implant delivery system 18 in partial section. A hollow member 20 having a distal tip 21 (which is preferably beveled or chamfered) defines hollow axial passage 25 (e.g. an axial lumen). Axial pusher 30 has a tip 35 that engages a corneal implant 15 that has been deformed in shape and constrained to fit inside the hollow axial passage 25 of the hollow member 20, as shown in FIG. 2B. The cross-section of hollow passage 25 may be circular, polygonal, or any other shape that is conducive to constraining the corneal implant 15. The hollow axial passage 25 of the hollow member 20 may contain ridges, protrusions, indentations, or recesses (now shown) which help to maintain orientation of the corneal implant as it advances distally of the hollow member (not shown). Axial pusher 30 engages one end of the constrained corneal implant 15 to advance the constrained implant through hollow passage 25. FIG. 2C shows the constrained corneal implant 15 emerging from a distal end of the hollow passage 25 still in its deformed and constrained configuration. By placing the tip of the hollow member 20 through an incision in the cornea, the corneal implant 15 may be advanced into the corneal pocket (not shown) through even a very small incision. In preferred aspects, the corneal implant is able to pass through an entry incision that is less than one-half the width of the corneal implant. In those cases, the hollow member will have an external width from 0.5 mm to 5 mm, preferably from 1 mm to 3 mm and an internal width from 0.3 mm to 4.8 mm, preferably from 0.8 mm to 2.8 mm.

Figure 3A:
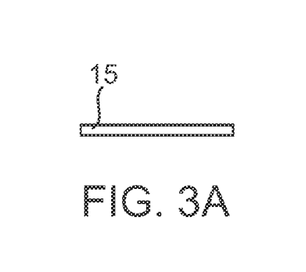
FIGS. 3A through 3C illustrate side views of a corneal implant as it is advanced and constrained by the apparatus of FIGS. 2A-2C.
Figure 3B:
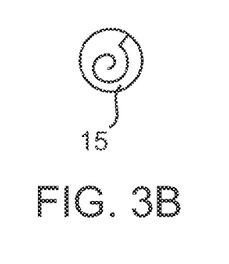
Figure 3C:
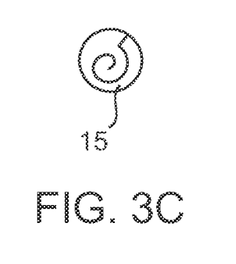

FIG. 3A shows a side view of corneal implant 15 in its non-deformed, non-constrained shape. FIGS. 3B and 3C shows an end on view of the corneal implant 15 as it is moved within the hollow member 20. Note that the corneal implant 15 has been deformed and constrained into a rolled configuration. The rolled configuration will preferably have a diameter in the range from 0.3 mm to 4.8 mm, more preferably from 0.6 mm to 2.6 mm, to fit into the hollow passage 25 of the hollow member 20.

Figure 4A:
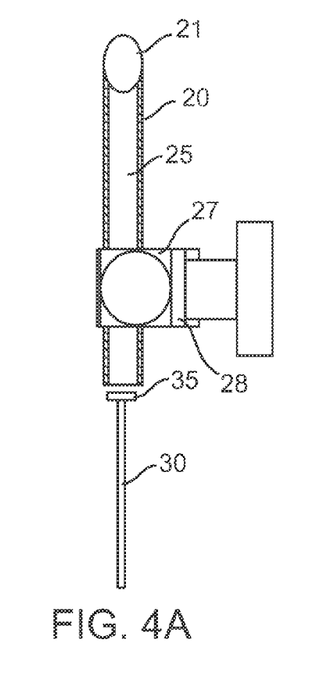
FIGS. 4A through 4D illustrate a second embodiment of the apparatus of the present invention.
Figure 4B:
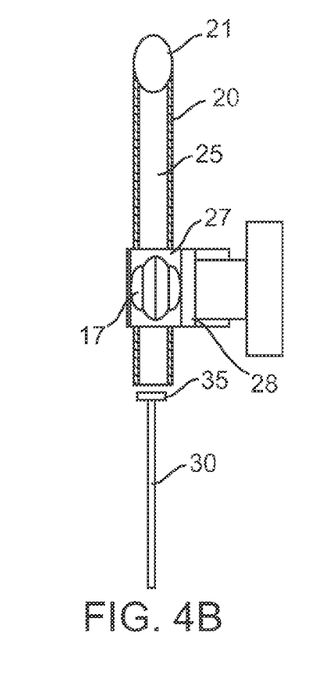
Figure 4C:
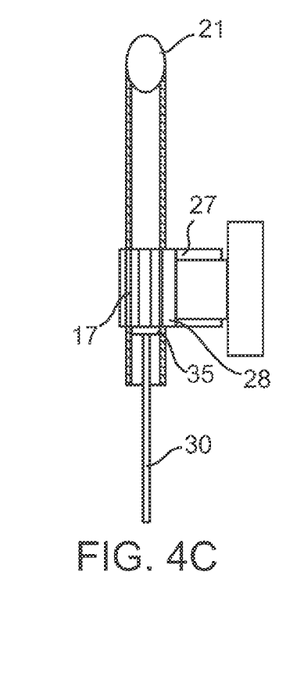
Figure 4D:
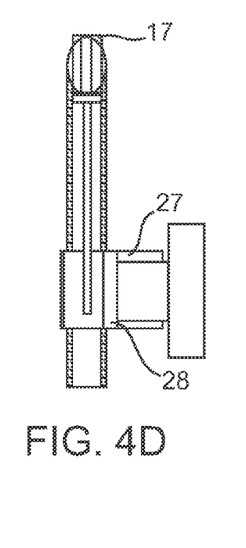
Figure 5A:
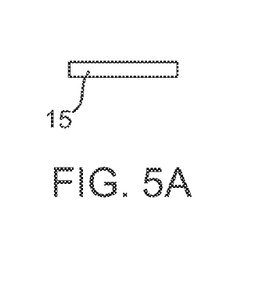
FIGS. 5A through 5D illustrate side views of a corneal implant as it is advanced and constrained by the apparatus of FIGS. 4A-4D.
Figure 5B:
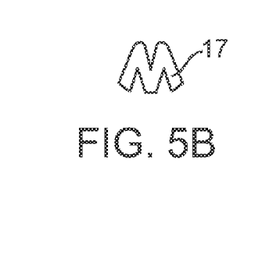
Figure 5C:
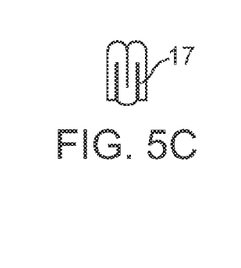
Figure 5D:
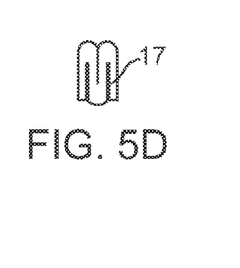

FIGS. 4A-4D shows a corneal implant delivery system with a deformation chamber 27 and a deforming member 28. In this embodiment of the invention, the corneal implant 15 is placed into the chamber 27 in an unconstrained and undeformed configuration and is then deformed into a folded or rolled corneal implant 17 within deformation chamber 27 by deforming member 28. Deforming member 28 is moved within deformation chamber 27 to deform and fold corneal implant 15 into a folded or rolled corneal implant 17. FIG. 4C shows axial pusher 30 engaging deformed corneal implant 17 by implant mover tip 35. FIG. 4D shows deformed and folded corneal implant 17. Axial pusher 30 engages corneal implant 17 to push the deformed constrained implant inside hollow passage 25. FIG. 4D shows that corneal implant 17 has been advanced by axial pusher 30 out of the hollow passage 25 while retaining a constrained shape. The constrained configuration of corneal implant 17 allows passage into the corneal pocket (not shown) through a small incision. The presence of the optional deformation chamber 27 and deforming member 28, advantageously allows the corneal implant 15 to be easily deformed into a configuration that will allow it to be placed through a small corneal incision into a corneal pocket.

FIGS. 5A-5D show side views of the corneal implant 15 being deformed into an exemplary deformed and folded or pleated corneal implant 17.

Figure 6A:
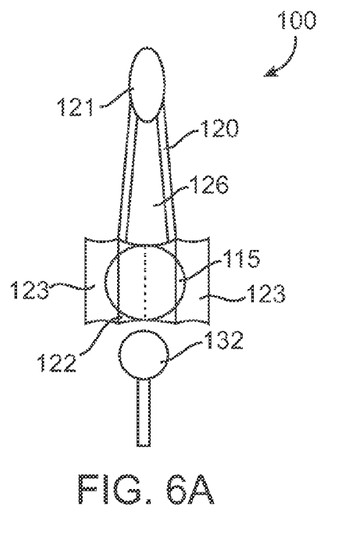
FIGS. 6A through 6C illustrate a third embodiment of the apparatus of the present invention.
Figure 6B:
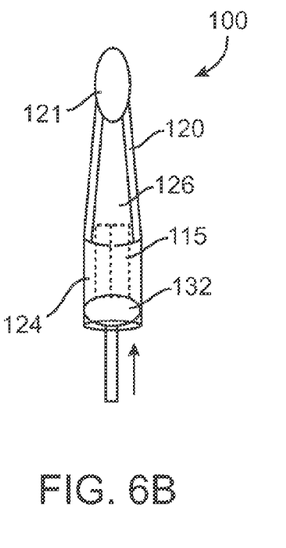
Figure 6C:
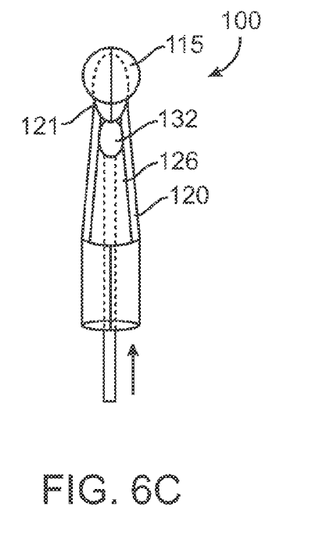

FIGS. 6A-6C show a top view of an alternative corneal implant delivery system 100. In this embodiment a corneal implant 115 is placed into a deformation area 122. When the "wings" 123 of the deformation area are closed, a deformation chamber 124 (FIG. 6B) is formed which deforms the corneal implant 115. In this embodiment, the corneal implant 115 is folded in half. A tip 132 of an axial pusher 130 engages corneal implant 115. The hollow member 120 is tapered so that hollow passage 126 is narrower at a distal end 121 that inserts into the corneal pocket. This allows the corneal implant 115 to be deformed into an even smaller cross-section as the implant is advanced distally and through the distal end 121. Advantageously in this embodiment, the implant mover tip 132 may also be deformable to fit within the narrowing hollow passage 126.

Figure 7A:
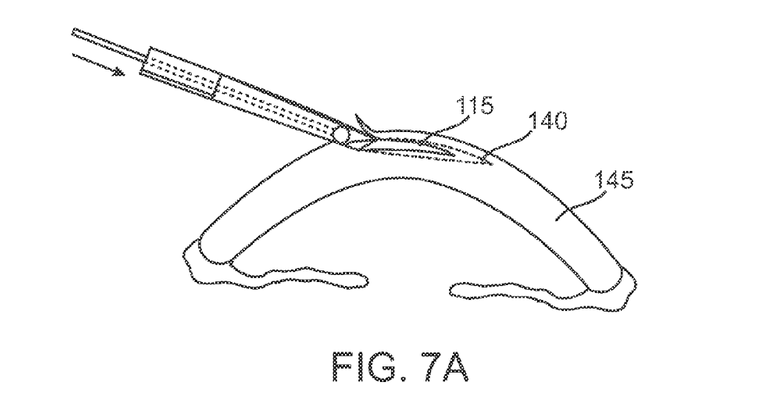
FIGS. 7A and 7B illustrate use of the apparatus of FIGS. 6A-6C in implanting an implant in a cornea.
Figure 7B:
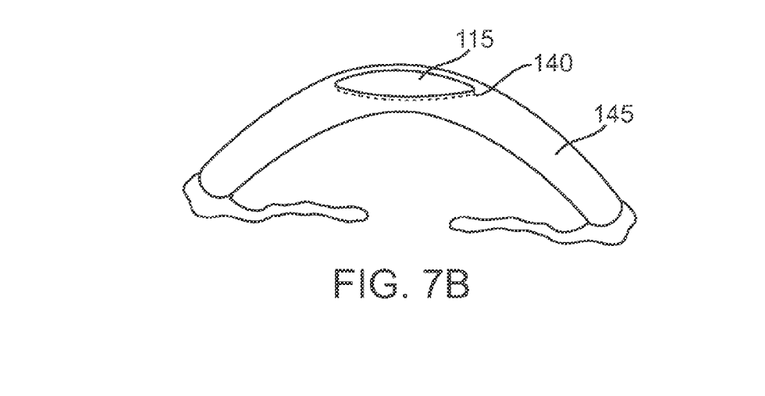

FIG. 7A shows a side cross-sectional view of corneal implant 115 being inserted into corneal pocket 140. FIG. 7B shows the final shape of corneal implant 115 after it has been inserted into corneal pocket 140 and unfurled or otherwise expanded back to its unconstrained size within cornea 145.

Figure 8A:
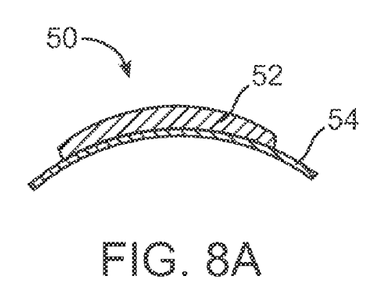
FIGS. 8A through 8D illustrate preferred corneal implants in accordance with the present invention.
Figure 8B:
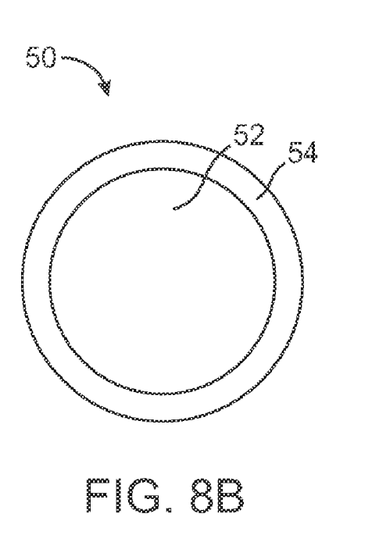

FIG. 8A illustrates a cross-sectional view of a corneal implant prosthesis 50 Corneal implant 50 is meant to replace a portion of the anterior layers of the cornea. In this embodiment there is a central optic 52 that protrudes anteriorly from a rim 54. In preferred aspects, the central optic would protrude anteriorly from the rim by 1 to 600 microns. More preferably, the central optic would protrude anteriorly from the rim by 50 to 400 microns. The central optic 52 will replace diseased anterior corneal tissue that has been removed. The rim 54 is designed to partly or fully around the center of optic and to fit within the peripheral recesses of a corneal pocket in order to anchor the corneal implant prosthesis to the cornea. The rim may be a continuous skirt as illustrated or may be crenellated or otherwise distributed in sections about the periphery of the center optic. FIG. 8B shows a top view of corneal implant prosthesis 50 which shows the central optic 52 and the rim 54. The rim 54 may optionally contain holes or be porous in nature so as to promote growth of corneal tissue into and through the implant, in order to promote retention and biocompatibility.

Figure 8C:
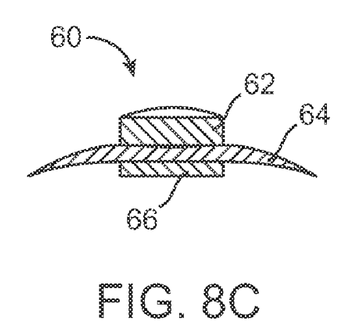
Figure 8D:
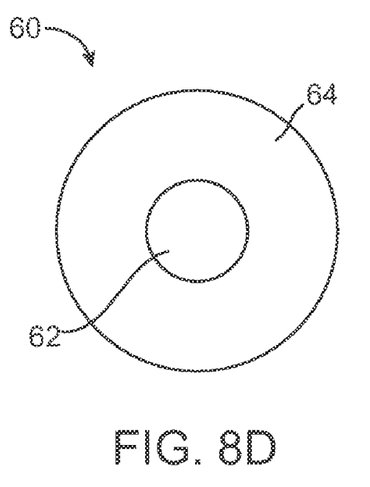

FIG. 8C shows a cross-sectional view of corneal implant prosthesis 60 which is meant to replace a full-thickness area of the cornea. In this embodiment there is an anterior portion of central optic 62 which protrudes anteriorly from a rim 64. The anterior portion of central optic 62 will replace diseased anterior corneal tissue that has been removed. In preferred aspects, the central optic would protrude anteriorly from the rim by 1 to 600 microns. More preferably, the central optic would protrude anteriorly from the rim by 50 to 400 microns. In addition corneal implant prosthesis 60 has a posterior portion of central optic 66 which protrudes posteriorly from rim 64. In preferred aspects, the central optic would protrude posteriorly from the rim by 1 to 900 microns. More preferably, the central optic would protrude posteriorly from the rim by 50 to 800 microns. The posterior portion of central optic 63 will replace diseased posterior corneal tissue that has been removed. The rim 64 will anchor corneal implant prosthesis 60 within the peripheral recesses of the corneal pocket and provide a water-tight seal. The rim 64 may optionally contain holes or be porous in nature so as to promote growth of corneal tissue into and through the implant, in order to promote retention and biocompatibility. The rim may be formed from any of the lens materials described above.

Figure 9A:
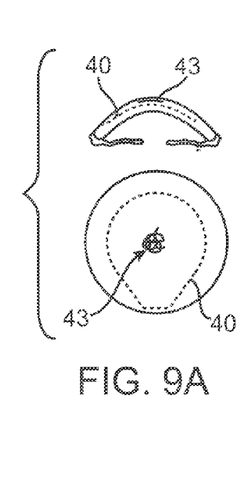
FIGS. 9A through 9F illustrate a further implantation protocol in accordance with the present invention.
Figure 9B:
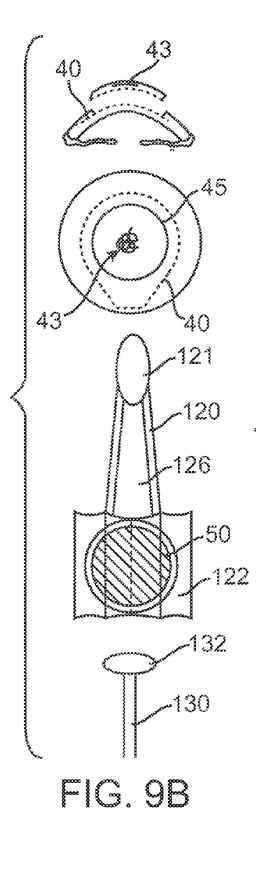
Figure 9C:
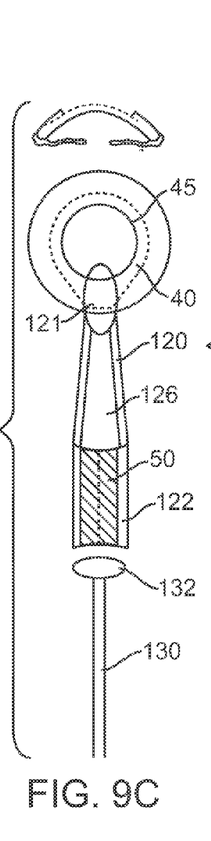
Figure 9D:
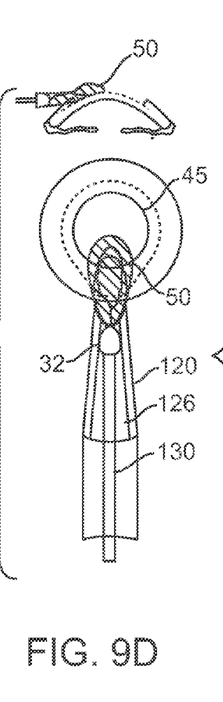
Figure 9E:
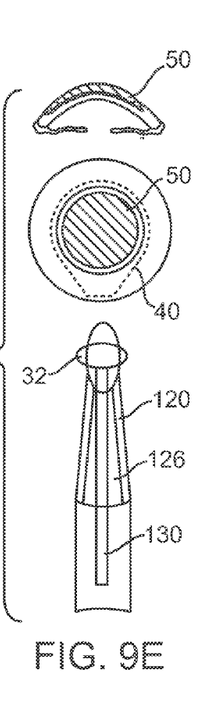
Figure 9F:
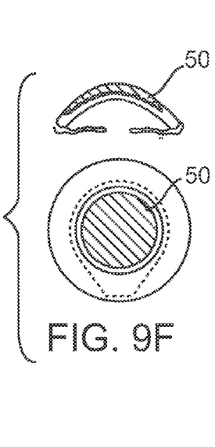

FIGS. 9A-9F show a method of treating an anterior corneal disease process using the methods and apparatus of the present invention. In each FIGS. 9A-F, a cross-sectional view of the cornea is seen above and a top view is seen below. In FIG. 9A it is shown that pocket 40 has been created posterior to anterior diseased cornea 43. FIG. 9B shows that anterior diseased cornea 43 has been excised with a circular trephine (not shown) to create an open top having a peripheral pocket. The edge of the excision is shown as 45. FIG. 9B also shows corneal implant 50 resting in the deformation area 122. In FIG. 9C the hollow member 120 has been inserted into pocket 40 through external opening 42 and corneal implant 50 has been folded in half within deformation chamber 124. FIG. 9D shows that corneal implant 50 has been further deformed into a more compact shape by its movement through narrowing hollow passage 126 and is being extruded into pocket 40. FIG. 9E shows that corneal implant 50 has been restored to its original shape within corneal pocket 40. Central optic 52 fills the space left by excised diseased anterior cornea 43 and restores optical clarity to the cornea. Hollow member 120 and implant mover 30 have been withdrawn from corneal pocket 40. FIG. 9F shows the final appearance of corneal implant 50 fixated within corneal pocket 40.

Figure 10A:
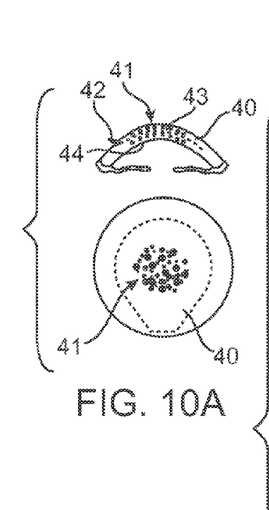
FIGS. 10A through 10F illustrate a further implantation protocol in accordance with the present inventions.
Figure 10B:
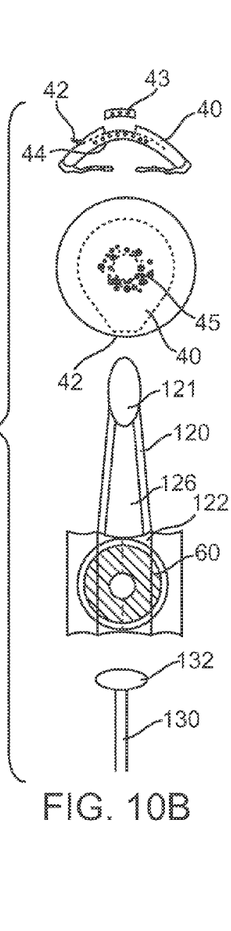
Figure 10C:
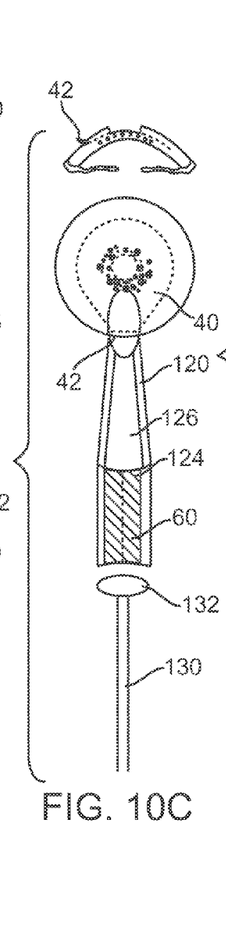
Figure 10D:
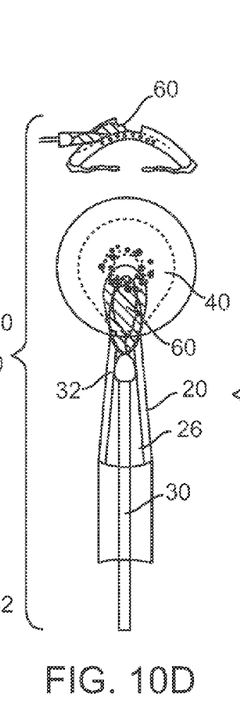
Figure 10E:
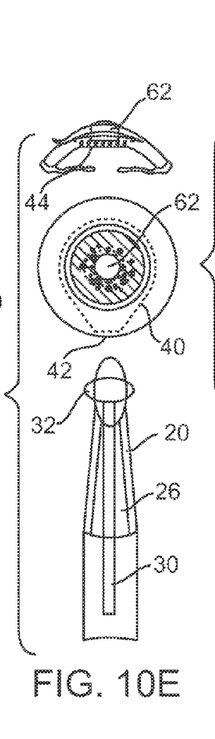
Figure 10F:
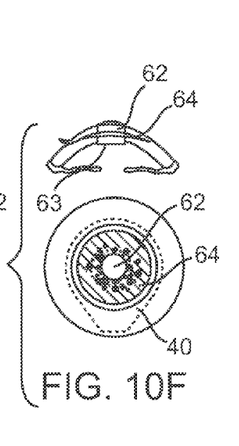

FIGS. 10A-10F show a method of treating a full-thickness corneal disease (e.g. pseudophakic bullous keratopathy) through the use of the present invention. In each FIGS. 10A-F, a cross-sectional view of the cornea is seen above and a top view is seen below. In FIG. 10A it is shown that pocket 40 has been created within the layers of the diseased cornea 41. The pocket divides the cornea into diseased anterior cornea 43 and diseased posterior cornea 44. FIG. 10B shows that anterior diseased cornea 43 has been excised with a circular trephine (not shown). The edge of the excision is shown in dashed lines as 45. FIG. 10B also shows corneal implant 60 resting in the deformation charter or area 122. In FIG. 10C the hollow member 120 has been inserted into pocket 40 through external opening 42 and corneal implant 60 has been folded in half within deformation chamber 122. FIG. 10D shows that corneal implant 60 has been further deformed into a more compact shape by its movement through narrowing hollow passage 126 and is being extruded into pocket 40. FIG. 10E shows that corneal implant 60 has been restored to its original shape within corneal pocket 40. Anterior optic 62 fills the space left by the excised diseased anterior cornea 43. In preferred aspects, after corneal implant 60 has been positioned in the pocket, the posterior diseased cornea 44 can be excised with low profile curved corneal scissors or some other cutting tool (e.g. plasma blade) inserted through external opening 42. FIG. 10F shows the final appearance of corneal implant prosthesis 60. Note that the rim 64 anchors corneal implant prosthesis 60 within the peripheral recesses of the corneal pocket and provides a water-tight seal. In this embodiment, posterior optic 63 protrudes through the space left by exicised diseased cornea 44. However, posterior optic 63 is optional and is not necessarily required for the corneal implant to properly function. It is to be understood that the relative dimensions, shapes, and angles of the anterior central optic 62, posterior central optic 63, and rim 64, may each be modified to promote improved retention as well as optical qualities all in keeping within the scope of the present invention.

Figure 11A:
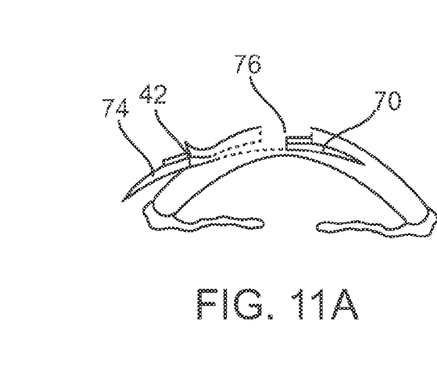
FIGS. 11A through 11F illustrate a further implantation protocol in accordance with the present inventions.
Figure 11B:
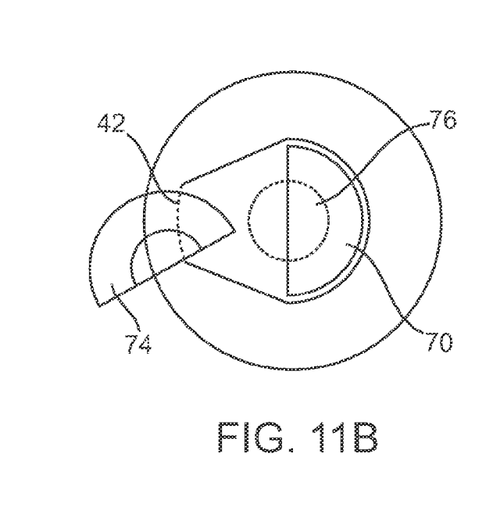
Figure 11C:
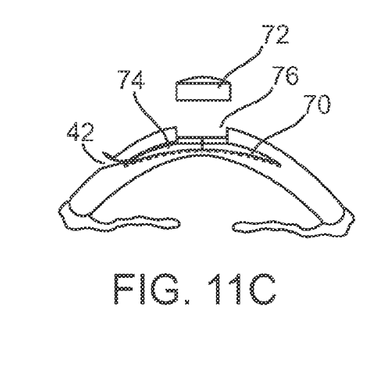
Figure 11D:
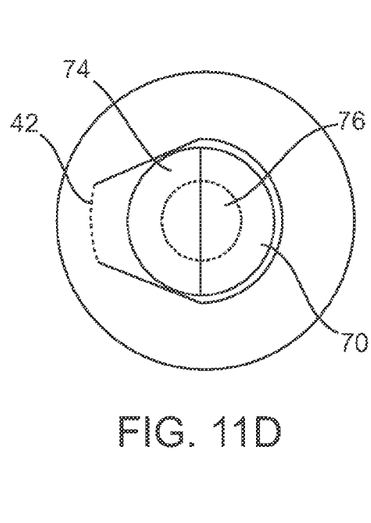
Figure 11E:
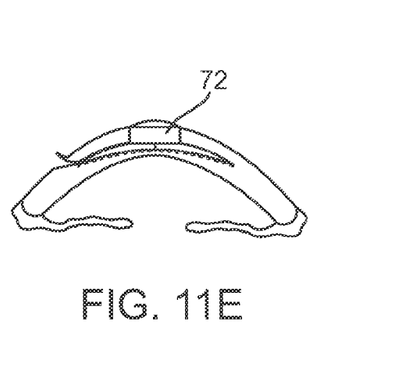
Figure 11F:
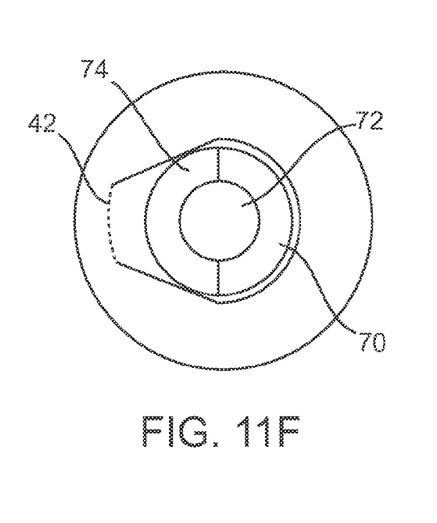

FIGS. 11A-11F show an embodiment of a corneal implant that can be assembled within the corneal pocket. By assembling individual smaller pieces of the corneal implant within the corneal pocket, a relatively large corneal implant can be constructed while using a relatively small external incision. The top portion of FIGS. 11A and 11B show a cross-sectional view of a cornea with an intra-stromal pocket. The bottom portion of FIG. 11A shows a top down view of a cornea with an intra-stromal pocket. In both FIGS. 11A and 11B, it can be seen that the first half of the rim 70 has already been inserted inside the pocket. A second half of the rim 74 is being inserted through the small external incision. Note that because the corneal tissue is partially elastic, the rim may be made of a relatively rigid material e.g. polymethylmethacrylate (PMMA) and still be inserted through the external opening 42 that is less than half of the diameter of the assembled corneal implant. The vertical dashed lines in the top of the figure and the circular dashed lines in the bottom figure represent an opening 76 left by a circular disk of anterior stromal tissue that has been excised (e.g. with a trephine). FIGS. 11C and 11D show that the optic 72 may fit into opening 76. FIGS. 11E and 11F show that the optic 72 has been attached to the two halves of the rim 70 and 74 to complete assembly of the corneal implant. The individual pieces of the corneal implant may be attached to each other by interlocking fittings (not shown), by glue, or any other appropriate mechanical or chemical method of fixation. In this embodiment of the invention the corneal implant is shown as a three piece prosthesis that replaces part of the cornea. However, it is to be understood that the invention includes any corneal implant that can be assembled as two or more pieces within a corneal pocket.

Figure 12A:
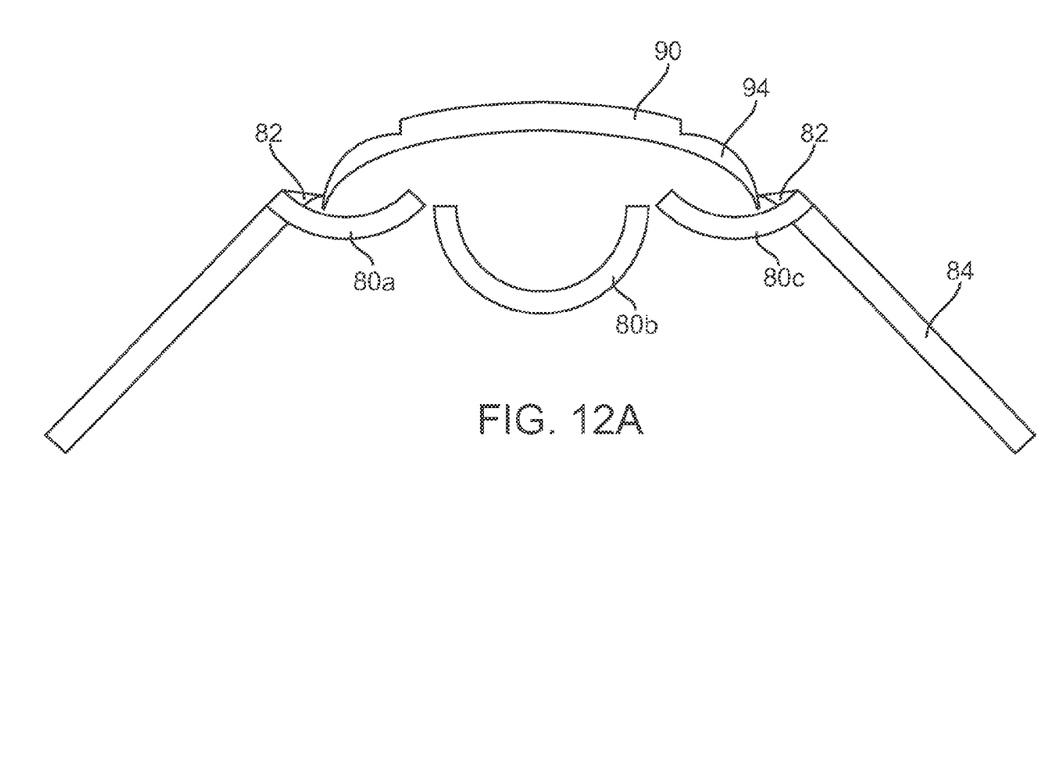
FIGS. 12A and 12B illustrate a tool in accordance with the principles of the present invention for collapsing and advancing a corneal implant.
Figure 12B:
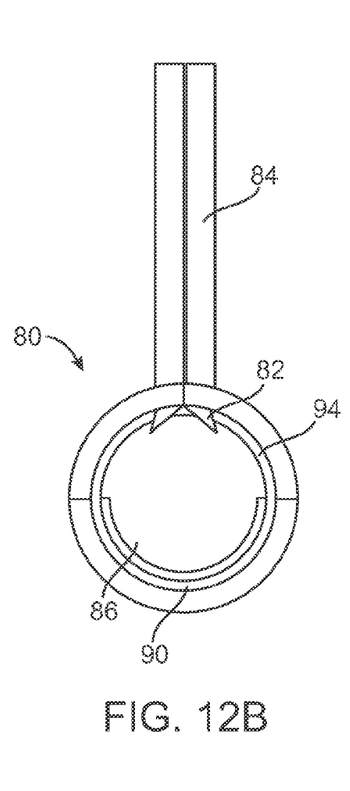

FIGS. 12A-12B are end views of the back of a deformation chamber 86 on a hollow member 80 which show how the presence of a protrusion 82 within the deformation chamber can help to maintain the orientation of a corneal implant 90 as it is pushed in an axial direction. Deformation chamber 86 includes three hinged sections 80a, 80b, and 80c which make up a hollow member which opens in order to receive corneal implant 90. At the lateral aspects of deformation area 80 are two protrusions 82, which help to hold the rim 94 of corneal implant 90 in place. FIG. 12B shows how sections 80a, 80b, and 80c can be closed by putting together the wings 84 (which together form an axial pusher or implant mover) to create hollow member 80 and deformation chamber 86. Corneal implant 90 is now securely fixated within the hollow deformation chamber 86 by the protrusions 82 and can be manipulated. The corneal implant 90 can then be moved axially along hollow member 80 by an axial pusher or other implant mover (not shown) without inadvertent rotation of the corneal implant.

Please note at least some portion of the corneal implant could be colored in any of the embodiments of the invention to enhance the aesthetic appearance of the eye or to decrease the amount of light exposure to the eye (e.g. for treatment of aniridia).

Figure 13A:
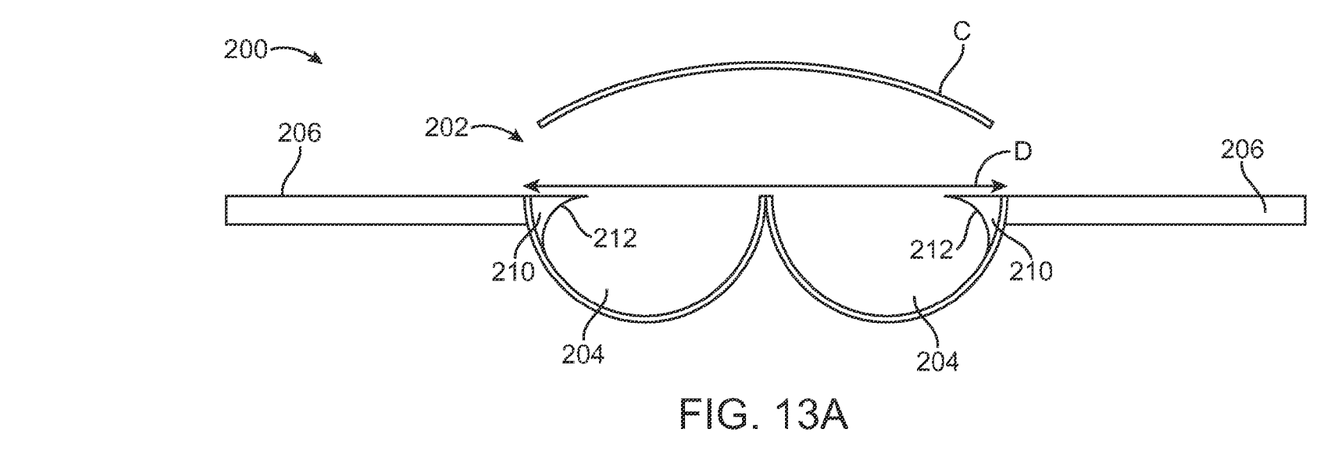
FIGS. 13A and 13B illustrate an alternative tool in accordance with the principles of the present invention for collapsing and advancing a corneal implant.
Figure 13B:
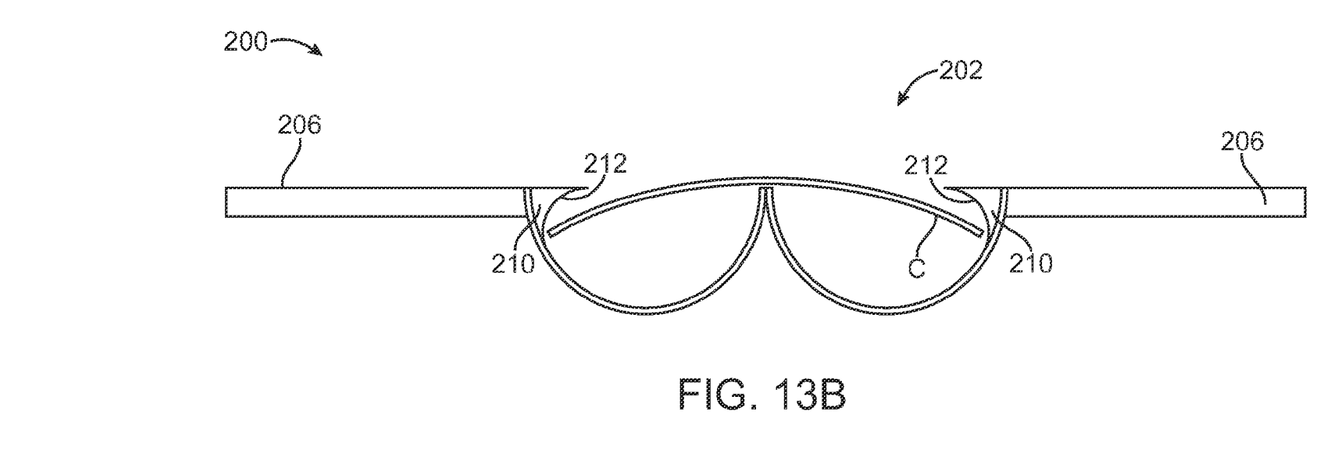

Referring now to FIGS. 13A and 13B, a corneal implant insertion device 200 includes a deformation chamber 202 defined by two-circular hinged sections 204. The hinged sections 204 are attached to wings 206 which permit the hinged sections to be closed in order to capture the corneal implant C, after the implant has been introduced into the deformation chamber, as shown in FIG. 13B.

Figure 14A:
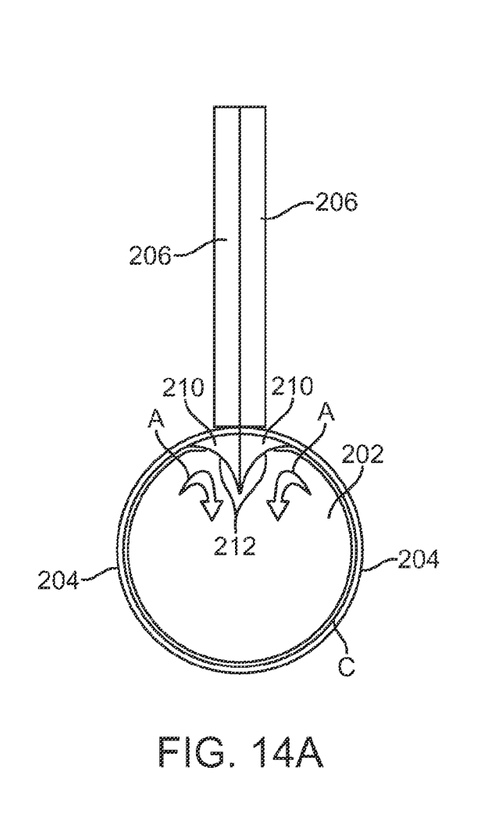
FIGS. 14A and 14C are cross-sectional views of the tool of 13A and 13B showing the implant as it is advanced as shown in FIGS. 15A through 15C.

Protrusions 210 having interior arcuate surfaces 212 are attached to the hinged sections 204 so that the surfaces 212 form radially inwardly directed ramps, as illustrated in FIG. 14A. Thus, after the corneal implant C is introduced into the deformation chamber 202, as illustrated in FIG. 13B, closure of the chamber using the wings 206 will curl the corneal implant C into a C-shaped profile, as shown in FIG. 14A. This can be an advantage over the corneal insertion tool embodiment of FIGS. 12A and 12B where the edges of the implant are held in a generally open configuration by the outwardly facing surfaces of protrusions 82.

In a specific embodiment of the corneal implant insertion device of the present invention, the corneal implant C comprises a lamellar corneal stromal endothelial transplant graft of approximately 9 mm in diameter and 100 µm in thickness. The deformation chamber 220 has a diameter or width D of approximately 9 mm in order to receive the corneal implant C such that its edges are disposed beneath the arcuate surfaces 212 of the protrusions 210, as illustrated in FIG. 13B.

Figure 15A:
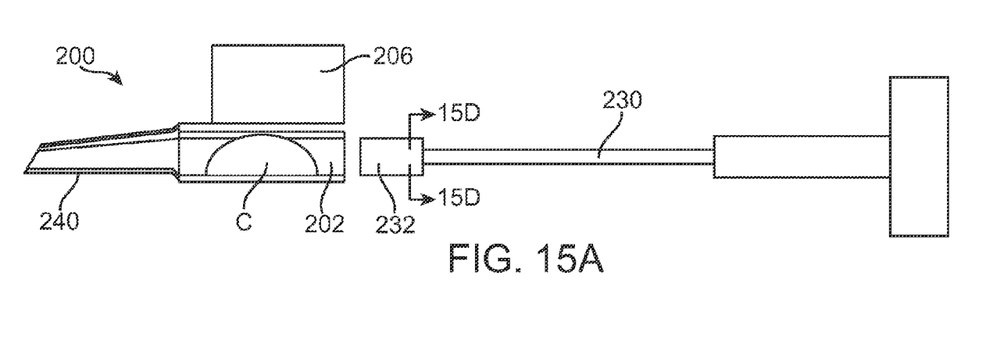
FIGS. 15A through 15D illustrate use of the tool of FIGS. 13A and 13B for advancing and reducing the cross-section of an implant in accordance with the principles of the present invention.
Figure 15B:
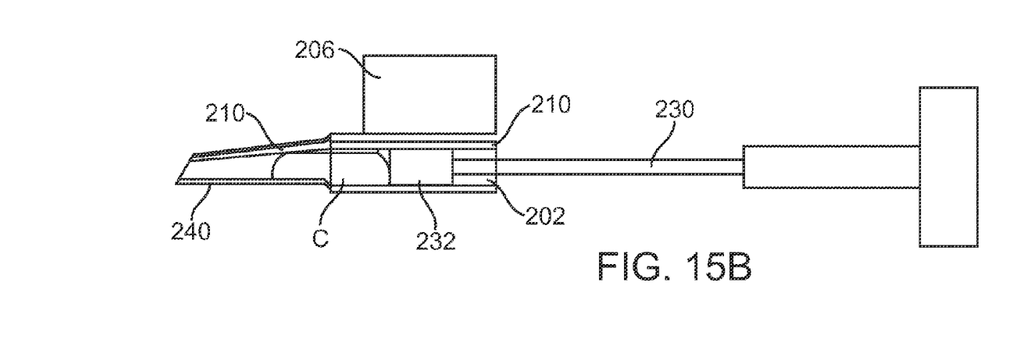
Figure 15C:
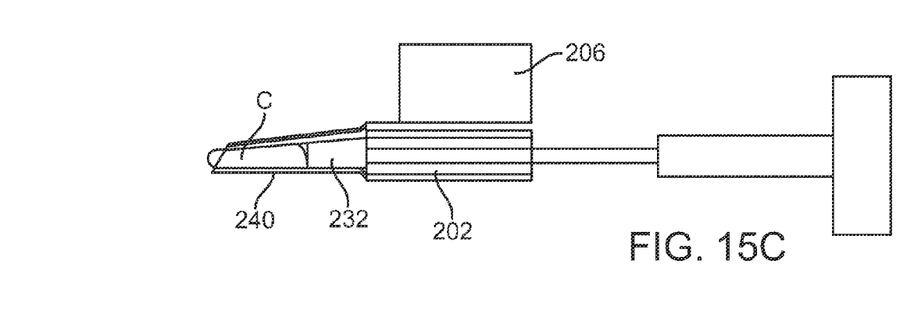
Figure 15D:
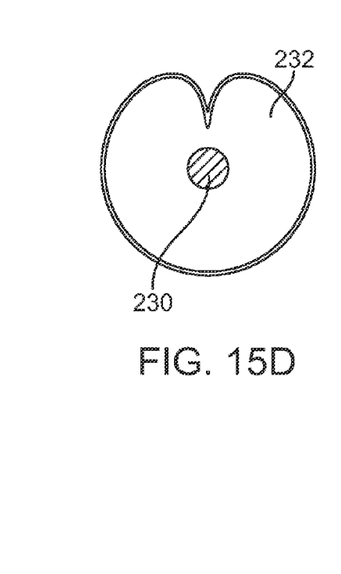

Referring now to FIGS. 15A through 15C, a pusher shaft 230 having a forward member 232 may be advanced into the deformation chamber 202 of the corneal implant insertion device 200. The forward element 232 will have a profile which is similar to the shape of the hollow passage so that it can pass over the protrusions 210 and will typically be compressible so that it can pass into a tapered region 240 of the insertion device, as shown in FIG. 15D. Thus, the forward member 232 will first be introduced into the constant-diameter portion of the deformation chamber 202, as shown in FIG. 15B, and used to advance the corneal implant C forwardly. The shaft 30 and forward member 232 will continue to be advanced so that the corneal implant C is pushed from the distal tip of the tapered region 240, as shown in FIG. 15C.

Figure 14B:
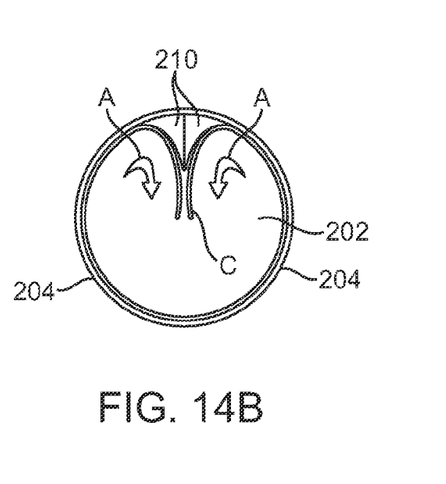
Figure 14C:
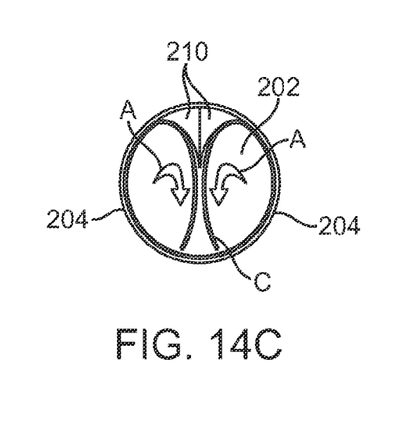

As the corneal implant C is advanced, its edges will be curved or everted inwardly, as illustrated in FIGS. 14A through 14C. In FIG. 14A, the corneal implant C is shown as it is in FIG. 15A. As it advances forwardly, as shown in FIG. 15B, the corneal implant C is reduced in diameter with the edges being pushed radially inwardly, as shown in FIG. 14B. Finally, as the corneal implant C is released from the proximal tip of the tapered region 240, it has a significantly reduced diameter, as shown in FIG. 14C. It is particularly desirable that the corneal implant C be reduced in size to as great an extent as possible but that the leading tips of the implant not touch the interior surface, just as shown in FIG. 14C. This reduces the damage or trauma to the delicate corneal endothelial cells during the implantation protocol.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A method for delivering a biological corneal implant having an exterior surface, an interior surface, and laterally opposed edges to a cornea, said method comprising:
   constraining the implant so that the laterally opposed edges evert inwardly to provide a C-shaped profile;
   advancing the implant through a chamber with a protrusion disposed between the laterally opposed edges to further evert the edges and reduce the width of the implant; and
   releasing the constrained biological corneal implant into the cornea or anterior chamber at the reduced width, wherein prior to release the laterally opposed edges of the biological corneal implant remain everted but do not touch the interior surface of the biological corneal implant such that damage to the implant is reduced.

2. A method as in claim 1, wherein constraining comprises closing semi-circular halves of a deformation chamber on the implant, wherein each half carries an inwardly directed ramp to evert the edges of the implant inwardly as the halves are closed.

3. A method as in claim 1, wherein advancing comprises pushing a pusher member against a rear edge of the corneal implant.

4. A method as in claim 3, wherein a forward portion of the pusher member conforms to the interior of the tapered chamber as the pusher member is pushed.

5. A method as in claim 1, wherein the biological implant comprises a lamellar corneal stromal endothelial transplant.

6. A method as in claim 1, wherein the protrusion extends over the entire length of the chamber and remains between the opposed edges until the constrained implant is released.

7. A method as in claim 6, wherein the chamber is tapered to a reduced width in the direction of advancement of the implant.

8. A system for delivering corneal implants, said system comprising:
   a deformation chamber having a proximal end, a distal end, and a pair of semi-circular halves hinged to each other along a common side, each semi-circular half having an inwardly oriented arcuate surface along an opposite side, said surfaces being adapted to evert opposite edges of an implant having an exterior surface and an interior surface when said implant is placed between the surfaces of the deformation chamber as the halves are closed;
   a hollow member having a proximal end and a distal end configured for insertion into a pocket within a cornea and having an axial hollow passage which tapers in the distal direction, wherein the axial hollow passage is attached to a distal end of the deformation chamber, receives the implant in an arcuate configuration, and includes inwardly oriented arcuate surfaces which further evert the opposite edges of the corneal implant radially inwardly as the insert is axially advanced through the passage, wherein the inwardly oriented arcuate surfaces of the hollow member are disposed on opposite sides of a protrusion which extends axially through the hollow passage to form inwardly directed ramps to curl the opposite edges of the implant into a C-shape wherein the opposite edges are everted but do not touch the interior surface of the implant as the implant is advanced; and
   an axial pusher disposed to be advanced through the deformation chamber and the hollow axial passage of the hollow member to engage and axially advance the corneal implant through the hollow passage.

9. A system as in claim 8, further comprising a corneal implant constrained within the deformation chamber on a distal side of the axial pusher.

10. A system as in claim 8, wherein the axial pusher is tapered in a distal direction.

11. A system as in claim 10, wherein the axial pusher is deformable so that it will reduce in diameter as it is distally advanced through the tapered hollow passage.

12. A system as in claim 11, wherein the axial pusher has a cross-sectional profile which is similar in shape to the cross-sectional profile of the deformation chamber and the hollow passage.

* * * * *